US00PP07789P

United States Patent [19]

Drewlow

[11] Patent Number: Plant 7,789

[45] Date of Patent: Feb. 11, 1992

[54] IMPATIENS PLANT NAMED INNOCENCE

[75] Inventor: Lyndon W. Drewlow, Ashtabula, Ohio

[73] Assignee: Mikkelsens, Inc., Ashtabula, Ohio

[21] Appl. No.: 607,021

[22] Filed: Oct. 31, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner

[57] ABSTRACT

A new and distinct cultivar of Impatiens plant named Innocence, characterized by its pure white flowers; mounded and highly self-branched habit; bright green leaves, a light reddish cast on the petioles and leaf stems; early blooming and floriferous habit; tolerance to both high and low temperatures and high sunlight; and its adaptability for growing in 10–25 cm pots.

1 Drawing Sheet

The present invention comprises a new and distinctive cultivar of Impatiens plant, botanically known as Impatiens, and referred to by the cultivar name Innocence. The new cultivar was developed by me through controlled breeding by crossing Mikkelsen Seedling No. 85-965-4 (seed parent) with Mikkelsen Seedling No. 86-290-1(pollen parent).

Asexual reproduction by terminal or stem cuttings has shown that the unique features of Innocence are stabilized and are produced true to type in successive propagations.

The following combination of characteristics distinguish Innocence from both its parent varieties and other cultivated Impatiens of this type known and used in the floriculture industry. Characteristics are described with refernce to the comparison cultivars Cirrus, disclosed in U.S. Plant Pat. No. 6,002, and Milkyway, disclosed in U.S. Plant Pat. No. 5,125. Color references are to The Royal Horticultural Society Color Chart (R.H.S.).

1. Innocence has a pure white flower (155C) while the flowers of Cirrus are 155A with a green tinge on the standard, and the flowers of Milkyway are 155D which, under cool conditions below 55° F. night temperatures, will have a pink blush which Innocence does not have.

2. Flower size of both Cirrus and Innocence is 4.5 to 5.0 cm in diameter, larger than the 4.0 to 4.5 cm flower diameter of Milkyway.

3. Lobing on the wing and keel flower petals of Innocence are deeper cut and the petals are not as rounded when compared to Milkway and Cirrus, both of which have round shallow cut petals.

4. Innocence has a mounded growth habit and is more highly self-branched than Cirrus and Milkyway, both of which are more upright in growth habit.

5. Innoncence has a light reddish cast to its stems which carries into the leaf petioles of mature leaves but not the midrib. Milkyway has a deep red cast to stems carrying into petioles and midrib. Cirrus has light green stems, petioles and midrib.

6. Innocence has a bright green leaf which is similar to Milkyway, while Cirrus has a dull green leaf. Under high light conditions, Innocence and Cirrus have more cream variegation around the midrib of the leaves than does Milkyway.

7. Innocence is 7 to 10 days earlier to bloom than Milkway, and 4 to 7 days earlier to bloom than Cirrus.

8. Innocence has fewer and longer ciliate on the leaf margin than either Milkyway or Cirrus.

9. Mature leaves of Innocence are longer (11–12 cm) than Cirrus (9–10 cm) and Milkyway (7–8 cm). The width of the leaves (3.0 to 3.5 cm) of Cirrus and Innocence is greater than the leaf width (2 to 2.5 cm) of Milkyway.

10. The flower pedicels of Innocence, when grown under high light conditions, have a light pink cast, while Cirrus has whitish green pedicels and Milkyway has a reddish cast to its flower pedicels.

11. Innocence and Milkyway have a 4.5 cm spur on a mature flower bud, while Cirrus has a much shorter spur (3.0 cm).

The accompanying colored photograph illustrates in front perspective view the overall appearance of Innocence and shows the colors as true as reasonably possible to obtain in a colored reproduction of this type. The photograph was taken in March 1990 under natural light on an overcast day under double poly greenhouse covering at Ashtabula, Ohio.

The following is a detailed description of Innocence, based on plants produced in greenhouses in Ashtabula, Ohio during the summer season of the year. Plants were grown in 15 cm pots and measurements were taken 16 weeks after rooted cuttings were planted. Height measurements were taken from the soil line of the container. The plants were grown as 65°–68° F. night temperatures, under 3500 to 4500 foot candles of light, and 240 ppm nitrogen, 240 ppm potassium, and 175 ppm phosphorous nutritional levels with trace elements added. Habit of growth, foliage coloration, leaf variegation, size of leaves and flower size will be greatly influenced by nutritional and environmental conditions. Color references are made to The Royal Horticultural Society Colour Chart (R.H.S.) except where general terms of ordinary dictionary significance are used.

Parentage: A controlled cross betwee female Mikkelsen Seedling No. 85-965-4 and male Mikkelsen Seedling No. 86-290-1.

Propagation:

A. *Type cutting.*—Stem 15 mm long will develop to 4 to 5 cm long in 18 to 21 days.

B. *Time to initiate roots.*—8–10 days at 23° C. summer; 10–12 days at 20° C. winter.

C. *Rooting habit.*—Heavy, fibrous.

Plant Description: Habit of growth, foliage coloration and size of leaf will be greatly influenced by nutritional and environmental conditions. Thus, data that follows was taken from plants grown under the conditions stated above.

A. *Form and habit of growth.*—Mounded; highly self-branch, intermediate in height; flowers over top of foliage; continuous flowering, vigorous growing, flowering herb.

B. *Foliage description.*—Bright dark green leaves with cream colored midrib and green venation on the underside of the leaves. Cream variegation around midrib increases in amount as light intensity increases. Under low light conditions leaves can be solid green.

1. Size: 11 to 12 cm long and 3 to 3.5 cm wide.

2. Shape: Lanceolate with acuminate apex and acute base. 3. Texture: Both upper and lower surfaces are glabrous.

4. Margin: Entire with fine ciliate.

5. Color: Young foliage top side, 146A; under side 146B. Mature foliage top side 147A; under side 147b.

6. Venation: Pinnate; green in color.

Flowering Description:

A. *Flowering habits.*—Flowers continuuosly from leaf whorl in a progressively orderly manner with one flower per leaf axil. When the last flower in a leaf whorl opens the first flower in the leaf whorl above opens. It takes 5 to 7 days for a mature bud to fully open, with flowers lasting two weeks or longer depending on the environment.

B. *Natural flowering season.*—Indeterminant and continuous. Quantity of flowering increases with increasing levels of light.

C. *Flower buds.*—Ellipsoidal, flowers perfect. Very light green spur (4.5 cm long) with pink cast under high light with yellow-green tip on a mature bud, with the throat behind the ovary and originating from the major sepal.

D. *Flowers borne.*—Individual white pedicels with faint green tinge from a whorl of 3 to 5 leaves, flowering progressively around the whorl as buds and leaves develop. Each leaf axial has one flower.

E. *Quantity of flowers.*—Very floriferous because of highly self-branching nature of plant and long lasting flowers with flowers open at two leaf whorls on a branch. Flower development is continuous and above leaf canopy.

F. *Diameter of flower.*—5 to 5.5 cm.

G. *Petals.*—1. Shape: Heart-shaped; two keel petals are larger than standard and wing petals. 2. Color: Top side when opening 155C with no fading; under side 155D. 3. Number of petals: Five.

4. Size of petals: Standard — 2.3 cm wide by 2.1 cm long; one lobe slightly large (1 mm), shallow cut. Wings — 1.5 cm wide by 2.5 cm long; lobes equal and deeper cut than standard. Keel — 2.2 cm wide by 3.0 cm long; lobes equal and similar cut as wings.

H. *Reproductive Organs.*—1. Stamens: Five in number. Anther shape is hooded; color white with very faint green cast; pollen color is cream. 2. Pistils: Stigma shape is five segmented column; color is cream with a touch of green. Style color is cream with a touch of green. Ovaries 5 in number, 3 mm in size, color is bright green.

Disease Resistance: No significant disease and insect problems noted to data. Innocence appears to be somewhat resistant to Botrytis under cool damp conditions.

Other Important Characteristics

1. Innocence has shown the ability to tolerate both high temperatures and high sunlight and continue to flower, while Milkyway and Cirrus tend to go out of flower under these conditions.

2. Innocence is much more tolerant to cool temperatures outside during spring and fall than Milkway and Cirrus. Thus, season can be extended.

3. Self-branching, early flowering nature allows Innocence to be grown in 10 cm pot. However, Innocence is also vigorous so that it can be grown in 15 to 25 cm containers as well.

4. Innocence usually has 3 to 4 leaves in a whorl while both Cirrus and Milkyway have 5.

I claim:

1. A new and distinct cultivar of Impatiens plant named Innocence, as illustrated and described.

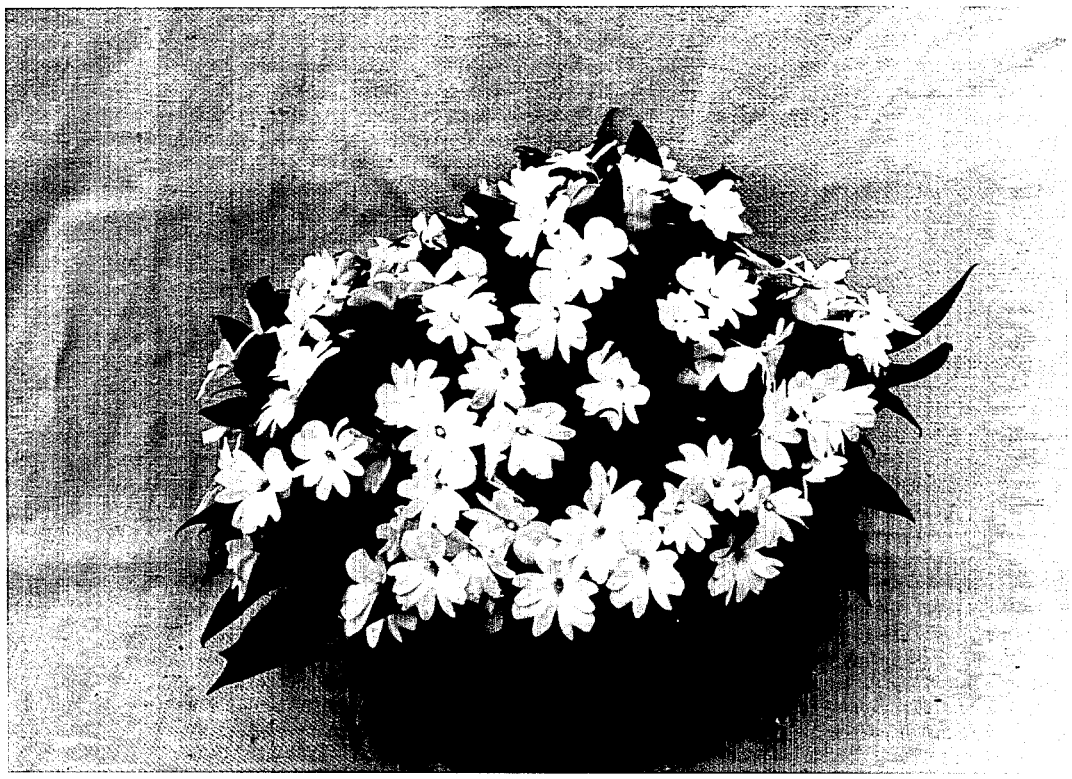

* * * * *